United States Patent [19]

Withjack

[11] Patent Number: 4,710,948

[45] Date of Patent: Dec. 1, 1987

[54] GEOLOGIC CORE HOLDER WITH COMPOSITE BARREL

[75] Inventor: Eric M. Withjack, Plano, Tex.

[73] Assignee: Atlantic Richfield Company, Los Angeles, Calif.

[21] Appl. No.: 808,766

[22] Filed: Dec. 13, 1985

[51] Int. Cl.[4] .............................................. H05G 1/00
[52] U.S. Cl. ........................................ 378/208; 73/38
[58] Field of Search ....................... 378/208, 4; 73/38

[56] References Cited

U.S. PATENT DOCUMENTS 3,897,345  7/1975  Foster .................................. 378/208

Primary Examiner—Stewart J. Levy
Assistant Examiner—Joseph W. Roskos
Attorney, Agent, or Firm—Michael E. Martin

[57] ABSTRACT

A geologic core holder includes an elongated barrel constructed of a composite of wound and longitudinally extending nonmetallic fibers embedded in a resin matrix to provide a high strength structure which presents minimal attenuation of x-rays and magnetic flux. The barrel has opposed end flanges and the core holder includes removeable end plugs which are slideable in a bore formed by the barrel. Opposed pairs of split retaining blocks are engageable with the end flanges for securing the end plugs in the barrel bore. One of the end plugs is adapted to support a flexible sleeve for holding the core sample within a cavity formed in the barrel bore whereby fluid pressure may be applied to exert a particular pressure and temperature condition on the core so that pressure fluid flow characteristics through the core may be studied and x-ray imaged.

9 Claims, 3 Drawing Figures

GEOLOGIC CORE HOLDER WITH COMPOSITE BARREL

BACKGROUND OF THE INVENTION

1. Field of the Invention

The present invention pertains to a core holder for testing the characteristics of geologic formation core samples.

2. Background

Geologic core holders have been developed of a type which permit testing the fluid flow characteristics of a geologic core sample at various temperature and pressure conditions. One deficiency of known types of core holders has been revealed as a result of the introduction of the use of computerized tomographic scanners for viewing the fluid flow patterns through various types of core samples under laboratory conditions. Metal core holders made of metals of high atomic number are particularly unsuitable in that the attentuation of the x-rays do not permit the use of these types of holders for producing computerized tomographic images. The substitution of metals of lower atomic numbers is unsuitable for many laboratory test conditions because of the pressure and temperature limitations at which metals such as aluminum may be used.

Accordingly, a profound need has been realized for the development of a geologic core sample holder which provides minimum attentuation of x-rays to permit the x-ray imaging of cores under various test conditions. There has also been a need to develop a core holder which will withstand the test pressures and temperatures needed to simulate actual subterranean formation environments and recovery processes which are likely to yield commercially viable quantities of hydrocarbons such as the West Sak and Ugnu oil fields in Alaska.

Still further, it has been recognized that the specialized use for a suitable core holder meeting the criteria mentioned above makes the cost of these structures relatively significant, and, accordingly, the need for a more versatile core holder suitable for operating under various conditions of core sample length and diameter, and core sample test conditions, has been particularly great. The need for an improved core holder has been recognized, not only in connection with the use of x-ray linear core scans and computerized tomographic scans, but magnetic measurements of core samples has also been viewed as requiring the use of non-magnetic core holders. Accordingly, the problems and desiderata associated with the development of an improved core holder have heretofore been unresolved but are largely met by the improved core holder of the present invention.

SUMMARY OF THE INVENTION

The present invention provides an improved device for holding geologic core samples and the like under various temperature and pressure conditions whereby various pressure and fluid flow tests may be performed and wherein linear and computerized tomographic x-ray images of a geologic core sample may be provided.

In accordance with one aspect of the present invention, there is provided an improved core holder having an outer housing in the form of a cylindrical barrel which is formed of a composite material which will permit operation of the core holder at temperatures and pressures greater than those permitted with core holders made of conventional non-magnetic metals while also permitting examination of a core sample under various pressure and temperature conditions by linear and computerized tomographic x-ray imaging. The composite construction of the core holder barrel may comprise circumferential windings and longitudinal extending strands of non-metallic filaments, such as glass or aramid fibers embedded in a resin matrix. In particular, the core holder barrel preferably also comprises an impermeable, corrosion resistant, inner liner on which is circumferentially wound a pretensioned layer of polymer-coated filaments, followed by a layer of tensioned longitudinally extending polymer coated filaments.

In accordance with another aspect of the present invention, there is provided an improved core holder having a generally cylindrical barrel made of a composite material having low x-ray attenuation characteristics and adapted to be connected to an improved retainer structure whereby removable end plugs, one of which may support the core sample within the holder barrel, are conveniently retained in assembly with the barrel to provide for substantially leak-proof testing of the core sample under various pressure and temperature conditions.

The improved core holder of the present invention may be used under a wide variety of core sample testing and examination conditions and wherein core samples of various lengths may be tested utilizing a single core holder structure.

Those skilled in the art will recognize additional features and advantages of the improved core holder of the present invention upon reading the detailed description which follows in conjunction with the drawing.

DESCRIPTION OF A PREFERRED EMBODIMENT

Figure 1:
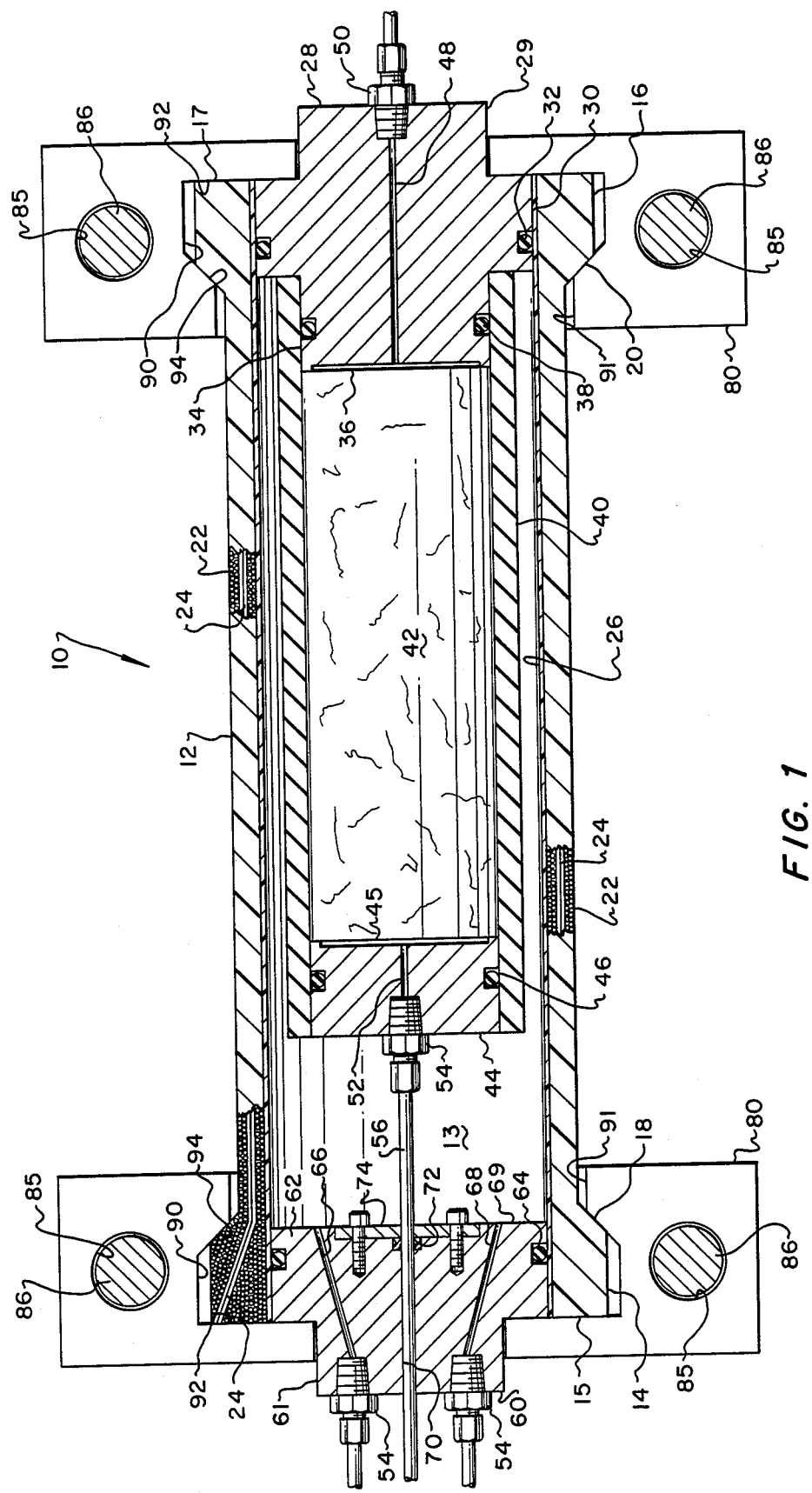
FIG. 1 is a longitudinal central section view of the improved core holder of the present invention.

In the description which follows, like parts are marked throughout the specification and drawing with the same reference numerals. The drawing figures are not necessarily to scale.

Referring to FIG. 1, there is illustrated a unique geologic core sample holder in accordance with the present invention and generally designated by the numeral 10. The core holder 10 is characterized by an elongated cylindrical barrel member 12 having opposed end flanges 14 and 16, respectively. The barrel 12 is characterized as a cylindrical tube wherein the flanges 14 and 16 are delimited by transverse planar end faces 15 and 17, and respective opposed inclined or frustoconical faces 18 and 20. The barrel 12 is advantageously constructed of a composite of non-metallic circumferentially wound filaments 22, as indicated by way of example, and longitudinally extending filaments 24. The filaments 22 and 24 are preferably pretensioned and are embedded in a resin matrix, preferably comprising a thermostat polymer having an oxygen to carbon linkage with a very dense, highly cross-linked molecular structure. One type of composite structure which may be used for the barrel 12 is manufactured under the trademark PYROITE by Tencom International, Inc., Avon, Ohio.

The filaments 22 and 24 are wound and laid in alternating layers, on an inner liner 26 which may be formed of a suitable plastic such as a fluorocarbon composition. In a typical example, a core holder having a barrel 12 of approximately 12.0 inches overall length, 3.70 inches outside diameter and 3.0 inches inside diameter, and manufactured of the abovedescribed composite materials, is suitable for working pressures of about 5000 psig at 250° F. Moreover, the very low attenuation of x-rays by the barrel 12 provides for use of a core holder having a barrel 12 wherein particularly high resolution x-ray images may be developed by a linear scanner or a tomographic type scanner.

The core holder 10 is further characterized by a first generally cylindrical end plug 28 having a cylindrical section 30 which is dimensioned to fit closely within the bore of the liner 26 and includes a suitable o-ring seal 32 to form a fluid type seal between the liner and the end plug. The end plug 28 includes a reduced diameter portion 34 delimited by an end face 36 and having a suitable o-ring seal 38 disposed on the circumference thereof and adapted to be in sealing engagement with an elongated, generally flexible cylindrical sleeve 40. The sleeve 40 is preferably formed of a suitably flexible material such as rubber, a urethane elastomer or fluoroplastic and is adapted to support a geologic core sample 42.

The end of the sleeve 40 opposite that connected to the plug 28 is closed by a removeable end plug 44 having an o-ring seal 46 disposed on the periphery thereof and in sealing engagement with the sleeve 40. The end plug 28 has a suitable passage 48 formed therein and opening to the end face 36. The passage 48 is also in communication with a suitable tube fitting 50 threaded into the outer end of the plug 28 at a second reduced diameter portion 29. The end plug 44 also has a passage 52 extending therethrough and opening to a transverse end face 45. The passage 52 is also in communication with a fitting 54 which is connected to an elongated fluid conducting tube 56.

The core holder 10 further includes a second end plug for the barrel 12, generally designated by the numeral 60. The plug 60 includes a cylindrical portion 62 having a diameter only slightly less than the inner diameter of the liner 26 and provided with suitable groove means for holding an o-ring type seal 64 on the periphery thereof whereby a fluid type seal is formed between the liner 26 and the plug 60. The plug 60 includes a reduced diameter portion 61 supporting spaced apart conventional conduit fittings 54 which are, respectively, in communication with internal passages 66 and 68 extending through the plug and opening to an end face 69. The plug 60 includes an elongated bore 70 for receiving the conduit 56 in slideable relationship thereto. A suitable fluid-tight packing 72 is disposed in a counterbore opening to the end face 69 and is retained by a removeable retainer plate 74.

Accordingly, an internal cavity 13, defined by the barrel 12 and the end plugs 28 and 60, is operable to receive pressure fluid through one or the other of the passages 66 and 68 wherein the other of the two passages may be used for bleeding air from the cavity 13 and/or used as a tap for a pressure guage or the like.

Moreover, fluids may be injected into the cavity containing the geologic core sample 42 through one or the other of the conduit 56 or the passage 48 with flow through the core sample 42 exiting the other of the two flow paths. In this way, the flow permeability and other characteristics of a geologic core may be tested for various types of fluids and at various pressures and temperatures.

Figure 2:
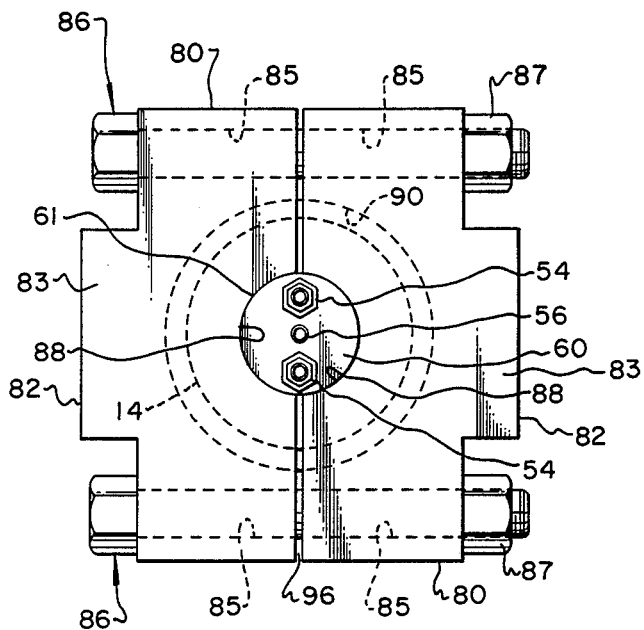
FIG. 2 is a transverse end view of one end of the core holder showing the configuration of one of the split end plug retainers for the core holder barrel.
Figure 3:
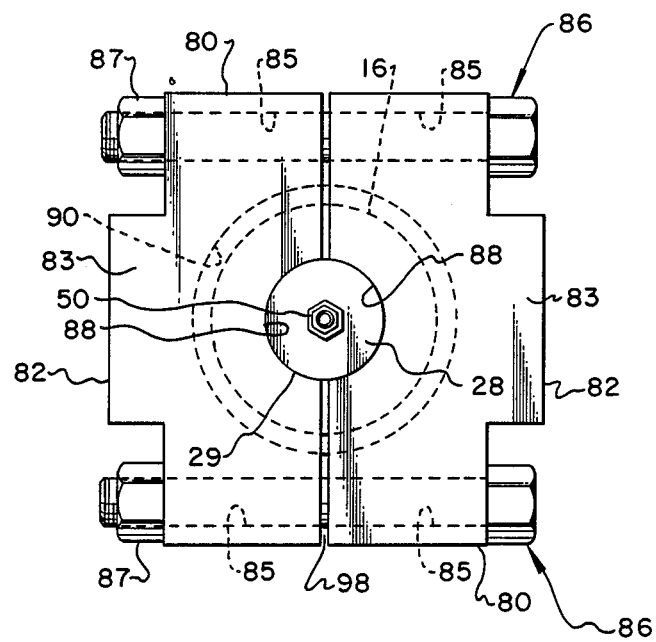
FIG. 3 is a transverse end view of the opposite end of the core holder.

Referring now to FIGS. 2 and 3 also, the core holder 10 includes an improved arrangement of retainer members for retaining the end plugs 28 and 60 in sealing engagement with the barrel 12. The retaining means for the plugs 28 and 60 comprise respective pairs of opposed retaining members 80 characterized as generally rectangular blocks, each having a support surface 82, defined by pedestal portions 83. The blocks 80 are also each provided with spaced apart parallel bolt receiving holes 85 for receiving threaded bolt assemblies 86 whereby the blocks 80 may, in pairs, be adapted to clamp to the respective barrel flanges 14 and 16 for retaining the respective plugs 60 and 28 in assembly with the barrel 12, as illustrated in FIG. 1. The blocks 80 each include a substantially semicircular clearance recess 88 to provide clearance around the reduced diameter portions 29 and 61 of the respective end plugs.

The blocks 80 also each include generally semicircular grooves 90 delimited by a transverse surface 92, FIG. 1, and an inclined surface 94 whereby the blocks may be clamped together by the bolt assemblies 86 and in assembly with the barrel 12 in wedging engagement with the inclined surfaces 18 and 20 of the respective barrel flanges. Clearance around the barrel 12 is also provided by generally semicircular recesses 91 which intersect the grooves 90 opposite the recesses 88. As illustrated in FIGS. 2 and 3, the retaining blocks 80, when in assembled relationship with the barrel 12, are dimensioned such that clearance gaps 96 and 98 are formed when respective pairs of retaining blocks 80 are assembled, as shown, to assure that a tight interfitting relationship occurs between the flanges 14 and 16 and the respective pairs of blocks.

The respective pairs of retaining blocks 80 serve as the sole means for retaining the end plugs 28 and 60 in the barrel 12 under the substantial fluid pressure forces which act on these plug members to eject them from the barrel. Any clamping forces acting on the barrel flanges 14 and 16 tending to collapse the barrel are opposed by the presence of the end plugs 28 and 60 themselves if the barrel undergoes elastic deformation in response to tightening of the bolt assemblies 86. Accordingly, the barrel 12 is not deformed and a fluid tight seal is assured between the respective plugs 28 and 60 and the bore formed by the liner 26. The retaining blocks 80 may be easily removed from the barrel 12 by merely unthreading the responsive nuts 87 of each of the bolt assemblies 86 and removing the retaining blocks by moving each block transversely with respect to the longitudinal central axis of the barrel 12 until sufficient clearance exists that the plugs 28 and 60 may be removed from the barrel.

For example, if it is desired to remove a core sample and replace it with another sample of different length or different geological characteristics, only the retaining blocks 80 which retain the end plug 28 are required to be removed from the barrel 12, whereupon the end plug 28, the core sample retaining sleeve 40 and the end plug 44 may be removed in assembly through the end of the barrel 12, normally closed by the plug 28, for interchanging a core sample or inspection thereof. The tube 56 is typically provided to be of sufficient length to permit withdrawal of the plugs 28 and 44 is assembly with the sleeve 40 out of the cavity 13 without disconnecting the tube 56 from the plug 44. After inspection of a core sample such as the core sample 42, or replacement thereof with another core sample, the plug 28 may be reassembled into the end of the barrel 12 and the pair of retaining blocks 80 securing the plug 28 may be reassembled and the bolt assemblies 86 tightened to securely clamp the blocks 80 to the barrel 12 and to retain the plug 28 within the barrel.

Thanks to the arrangement of the opposed flanges 14 and 16 on the barrel 12, including the inclined surfaces 18 and 20 which are engageable with the inclined grooved surfaces 94, the barrel 12 is not unduly stressed at its opposite ends by forces due to assembly of the end plug retaining means with the barrel 12. Accordingly, the arrangement of the retaining blocks 80 not only provides for ease of assembly and disassembly of the core holder 10 but reduces stresses on the barrel 12 which might tend to aggravate the total stress on the barrel under certain working pressures and temperatures and reduce the actual working load capability of the barrel.

The operation of the core holder 12 is believed to be readily understandable from the foregoing description. Detailed descriptions of the various pressure fluid flow lines and sources adapted to be connected to the passages 66, 68 and 48, as well as the conduit 56, have been omitted in the interest of clarity and conciseness. Moreover, those skilled in the art will recognize that multiple passages may be provided in the end plug 28, for example, for use in injecting more than one fluid and/or for measuring pressures within the cavity containing the core sample 42 during test conditions. Thanks to the provision of the composite construction of the barrel 12, the core holder 10 advantageously provides for high quality x-ray imaging of the geologic core sample 42 under various pressures and temperatures as well as various fluid flow conditions imposed on the core sample.

Although a preferred embodiment of the present invention has been described in detail herein, those skilled in the art will recognize that various substitutions and modifications may be made to the core holder 10 without departing from the scope and spirit of the present invention as recited in the appended claims.

What I claim is:

1. A core holder for testing geologic core samples including x-ray imaging of said core samples under various test conditions comprising:
   an elongated cylindrical barrel adapted to provide minimal attenuation of x-rays when subjected to x-radiation, said barrel comprising a composite of wound non-metallic filaments embedded in a thermoset polymer resin matrix and said barrel including opposed ends;
   opposed removeable end plugs insertable in a bore formed by said barrel and defining a cavity for receiving a geologic core sample, one of said plugs including means for supporting said core sample within said bore; and
   plug retaining means engageable with said barrel at opposite ends thereof for retaining said plugs in said bore, respectively.

2. The core holder set forth in claim 1 wherein:
said barrel includes opposed radially extending flange means at opposite ends of said barrel and said retaining means comprises a pair of opposed retaining blocks for at least one end of said barrel, said blocks each being engageable with said flange means, and fastening means for securing said retaining blocks to said barrel for retaining one of said plugs in said blocks.

3. The core holder set forth in claim 2 wherein:
said flange means each define a transverse endface of said barrel, and said flange means include an inclined surface opposite said endface and delimiting said flange means, and said retaining blocks each include groove means for receiving said flange means for interfitting said blocks with said barrel and for retaining said one plug in assembly with said barrel.

4. The core holder set forth in claim 3 wherein:
each of said retaining blocks includes a substantially semi-circular groove defining said groove means for receiving a portion of said flange means whereby said barrel may be clamped between opposed ones of said retaining blocks.

5. The core holder set forth in claim 4 wherein:
said one plug includes an enlarged diameter portion having a diameter only slightly less than the diameter defining a bore of said barrel whereby said one end plug may be slideably received in said bore and retained therein by said retaining blocks.

6. The core holder set forth in claim 4 wherein:
said one plug includes means for supporting an elongated flexible sleeve for disposition in said bore of said barrel, said sleeve supporting a geologic core, and a closure plug disposed in the opposite end of said sleeve for retaining said core within said sleeve.

7. A core holder for testing geologic cores including at least one of x-ray imaging and magnetic flux measurement of said cores under various test conditions comprising:
   an elongated cylindrical barrel adapted to minimize the attenuation of x-radiation and magnetic flux and comprising a composite of wound non-metallic filaments embedded in a thermoset polymer resin matrix, said barrel including opposed ends;
   opposed end plugs closing a bore formed by said barrel and defining a cavity for receiving a geologic core, one of said plugs including means for supporting said core within said bore, said one plug including a portion having a diameter only slightly less than the diameter of said bore of said barrel whereby said one plug may be slideably received in said bore; and
   plug retaining means engageable with said barrel and comprising a pair of opposed retaining blocks engageable with said barrel, said retaining blocks each being engageable with fastening means for securing said retaining blocks to said barrel for retaining said one plug in said bore.

8. The core holder set forth in claim 7 wherein:
said barrel includes flange means defining a transverse endface of said barrel, said flange means including an inclined surface opposite said endface and delimiting said flange means, and said retaining blocks each include groove means for receiving said flange means for interfitting said blocks with said barrel and for retaining said one plug in assembly with said barrel.

9. A core holder for use in x-ray imaging of geologic cores comprising:
- an elongated cylindrical barrel member adapted to minimize the attenuation of x-radiation and magnetic fluid imposed on said barrel member, said barrel member forming a cylindrical bore and having opposed radially outwardly projecting end flanges, and said barrel member being constructed of a composite of circumferentially wound and longitudinally extending elongated non-metallic filaments embedded in a thermoset polymer resin matrix;
- opposed end plugs forming closures for said bore, each of said end plugs including a cylindrical portion adapted to be disposed in close fitting slideable relationship in said bore and including seal means for providing a fluid-tight seal between said barrel member and said end plugs, respectively;
- at least one of said end plugs including means for supporting a geologic core in said bore of said barrel member whereby said core may be subjected to various conditions of fluid pressure and temperature imposed on said core; and
- retaining means for each of said end plugs, said retaining means including respective pairs of opposed retaining blocks, each of said retaining blocks including means defining a groove for receiving at least a portion of one of said flanges and a transverse end face engageable with one of said end plugs for retaining said one end plug in said bore; and
- fastening means for securing said retaining blocks to each other in opposed pairs for securing said retaining blocks to said barrel member and so as to retain said end plugs in said bore, respectively.

* * * * *